US009060230B2

(12) United States Patent
Michel et al.

(10) Patent No.: US 9,060,230 B2
(45) Date of Patent: Jun. 16, 2015

(54) EAR CLEANING APPARATUS

(71) Applicants: Florent Michel, Annemasse (FR); Raphael Michel, Palo Alto, CA (US); Daniel Shen, Stanford, CA (US)

(72) Inventors: Florent Michel, Annemasse (FR); Raphael Michel, Palo Alto, CA (US); Daniel Shen, Stanford, CA (US)

(73) Assignee: ARIA INNOVATIONS, INC., Mountain View, CA (US)

( * ) Notice: Subject to any disclaimer, the term of this patent is extended or adjusted under 35 U.S.C. 154(b) by 0 days.

(21) Appl. No.: 14/291,424

(22) Filed: May 30, 2014

(65) Prior Publication Data

US 2014/0294213 A1 Oct. 2, 2014

Related U.S. Application Data

(63) Continuation of application No. 13/865,717, filed on Apr. 18, 2013, now Pat. No. 8,577,067, and a continuation of application No. 12/841,120, filed on Jul. 21, 2010, now Pat. No. 8,457,337.

(51) Int. Cl.

| | |
|---|---|
| ***A61F 9/00*** | (2006.01) |
| ***H04R 25/02*** | (2006.01) |
| *H04R 1/42* | (2006.01) |
| *H04R 25/00* | (2006.01) |

(52) U.S. Cl.

CPC *H04R 25/02* (2013.01); *H04R 1/42* (2013.01); *H04R 25/456* (2013.01); *H04R 25/606* (2013.01); *H04R 25/652* (2013.01); *H04R 2460/09* (2013.01); *H04R 2460/11* (2013.01); *H04R 2460/13* (2013.01); *H04R 2460/17* (2013.01); *H04R 25/656* (2013.01); *H04R 25/658* (2013.01)

(58) Field of Classification Search

USPC .......................................................... 381/328

See application file for complete search history.

(56) References Cited

U.S. PATENT DOCUMENTS

| | | | | |
|---|---|---|---|---|
| 5,572,594 | A * | 11/1996 | Devoe et al. | 381/328 |
| 6,033,417 | A * | 3/2000 | Tseng | 606/162 |
| 2005/0096678 | A1* | 5/2005 | Olson | 606/162 |
| 2006/0085018 | A1* | 4/2006 | Clevenger | 606/162 |
| 2007/0009106 | A1* | 1/2007 | Tilson et al. | 381/60 |
| 2012/0296355 | A1* | 11/2012 | Burres | 606/162 |
| 2014/0052163 | A1* | 2/2014 | Lai | 606/162 |

* cited by examiner

*Primary Examiner* — Christopher Uhlir
(74) *Attorney, Agent, or Firm* — Francis Law Group

(57) ABSTRACT

The invention provides apparatus and methods for cleaning an ear canal. The ear cleaning apparatus includes an elongated support member having an outer surface and first and second ends, and a bristle member that is attached to one end of the support member. The bristle member includes a plurality of flexible elongated members that are configured to contact a surface of an ear canal when the support member/bristle member assembly is inserted into the ear canal.

4 Claims, 8 Drawing Sheets

EAR CLEANING APPARATUS

CROSS-REFERENCE

This application is a continuation of U.S. application Ser. No. 13/865,717, filed Apr. 18, 2013, which is a continuation of U.S. application Ser. No. 12/841,120, filed Jul. 21, 2010, now U.S. Pat. No. 8,457,337, which claims the benefit of U.S. Provisional Application No. 61/227,437, filed Jul. 22, 2009, U.S. Provisional Application No. 61/228,571, filed Jul. 25, 2009, and U.S. Provisional Application No. 61/228,588, filed Jul. 26, 2009.

BACKGROUND OF THE INVENTION

Early generation hearing devices were primarily of the Behind-The-Ear (BTE) type, where an externally mounted device was connected by an acoustic tube to a molded shell placed within the ear. With the advancement of component miniaturization, modern hearing devices rarely use this Behind-The-Ear technique, focusing primarily on one of several forms of an In-The-Canal hearing device. Three main types of In-The-Canal hearing devices are routinely offered by audiologists and physicians. In-The-Ear (ITE) devices rest primarily in the concha of the ear and have the disadvantages of being fairly conspicuous to a bystander and relatively bulky to wear. Smaller In-The-Canal (ITC) devices fit partially in the concha and partially in the ear canal and are less visible but still leave a substantial portion of the hearing device exposed. Recently, Completely-In-The-Canal (CIC) hearing devices have come into greater use. As the name implicates, these devices fit deep within the ear canal and are essentially hidden from view from the outside.

In addition to the obvious cosmetic advantages these types of in-the-canal devices provide, they also have several performance advantages that larger, externally mounted devices do not offer. Placing the hearing device deep within the ear canal and proximate to the tympanic membrane (ear drum) improves the frequency response of the device, reduces distortion due to jaw extrusion, reduces the occurrence of the occlusion effect and improves overall sound fidelity.

The shape and structure, or morphology, of the ear canal varies from person to person. Since the morphology of the ear canal varies so greatly from person to person, hearing aid manufacturers and audiologists have traditionally employed custom manufactured devices in order to precisely fit the dimensions of each user's ear canal. This frequently necessitates impressions of the user's ear canal to be taken. The resulting mold is then used to fabricate a rigid hearing device shell. This process is both expensive and time consuming and the resulting rigid device shell does not perform well during the deformations of the ear canal shape that occurs during normal jaw movement. In order to receive a properly fit hearing device, the user typically has to make several trips to the audiologist for reshaping and resizing. Even after the best possible fit is obtained, the rigid shell rarely provides comfortable hearing enhancement at all times.

Flexible earmolds for hearing devices have been considered. See, e.g., U.S. Pat. No. 5,979,589 and U.S. Pat. No. 7,362,875, which are hereby incorporated by reference in their entirety. However, these traditional earmolds often provide poor ventilation, often forming airtight contact within ear canals. Traditional earmolds may also push earwax into the ear. Also, while such earmolds provide some flexibility in fitting into varying ear canals, they do not provide optimum alignment and adaptability to a wide degree of variations in ear canal shapes.

Therefore, a need exists for improved hearing devices which are able to conform to various ear canals and are comfortable.

SUMMARY OF THE INVENTION

An aspect of the invention provides an open ear canal hearing aid comprising: an electronics containing portion; and a bristle assembly connected to the electronics containing portion, wherein the bristle assembly is configured to secure the hearing aid within an ear canal. Another aspect of the invention is directed to open ear canal hearing aid comprising: an electronics containing portion; and a passive amplifier connected to the electronics containing portion.

In accordance with another aspect of the invention, an open ear canal hearing aid may comprise an electronics containing portion; a passive amplifier connected to the electronics containing portion; and a bristle assembly covering at least a portion of the electronics containing portion or the passive amplifier.

A hearing aid may be provided in accordance with another aspect of the invention, wherein the hearing aid comprises an electronic component-containing portion; a passive amplifier connected to the electronic component-containing portion; and an adjustable securing mechanism covering at least a portion of the electronic component-containing portion configured to contact an ear canal surface when the hearing aid is in use, and providing at least one air flow path through the hearing aid or between the hearing aid and ear canal surface.

Another aspect of the invention provides a method for using a hearing aid comprising: inserting at least a portion of a hearing aid having a securing mechanism and an amplifier into an ear canal so that at least a portion of the securing mechanism contacts the ear canal surface and an air channel is formed through the hearing aid or between the hearing aid and ear canal; and adjusting the securing mechanism from a first position to a second position.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The invention provides open ear canal hearing aids with securing mechanisms. Various aspects of the invention described herein may be applied to any of the particular applications set forth below or for any other types of hearing device or ear cleaning device. The invention may be applied as a standalone system or method, or as part of a hearing assistance system or method. It shall be understood that different aspects of the invention can be appreciated individually, collectively, or in combination with each other.

Figures provided herein may or may not be provided to scale. The relative dimensions or proportions may vary. The hearing devices may be sized to fit within an ear canal of a subject. In some embodiments, the hearing device may be on the order of about 1 mm, 5 mm, 1 cm, 1.5 cm, 2 cm, 2.5 cm, 3 cm, 3.5 cm, 4 cm, 5 cm, 6 cm, or 7 cm long.

Figure 1:
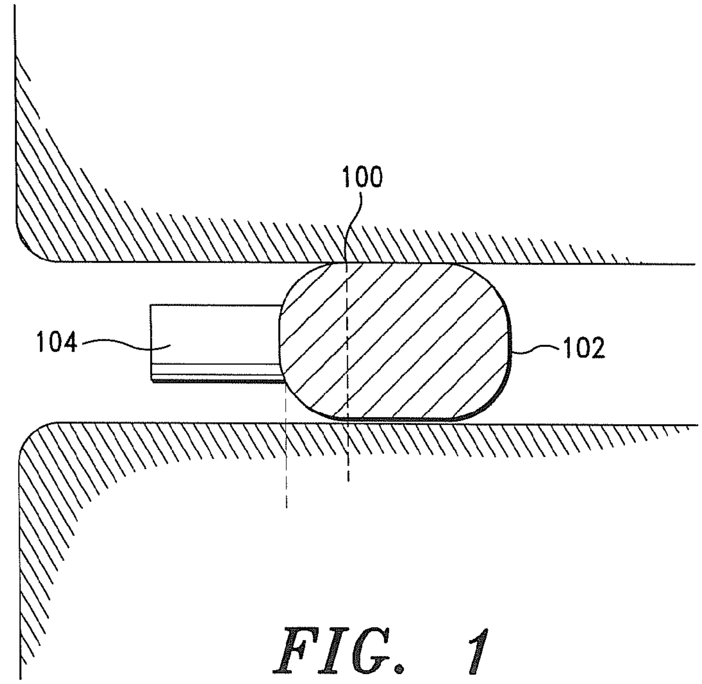
FIG. 1 shows a hearing aid provided in an ear canal in accordance with an embodiment of the invention.

FIG. 1 shows a hearing aid provided in an ear canal in accordance with an embodiment of the invention. In some embodiments, the hearing aid may be provided entirely within the ear canal. Alternatively, a portion of the hearing aid may be external to the ear canal and a portion of the hearing aid may be within the ear canal. The hearing aid may transmit and amplify sound using a flexible interface that may or may not come in contact with the eardrum and/or ear canal. This interface may be soft, atraumatic for the eardrum. This hearing aid, including the interface, may sit in the external ear canal. The flexible interface may be entirely within the ear canal, or a portion of the flexible interface may be external to the ear canal.

In some embodiments, one or more portion of the hearing aid may come in contact with the surface of the ear canal. In some embodiments, a flexible interface may come into contact with the ear canal surface. The hearing aid may contact 100 a portion of the ear canal that may allow bone conduction. The hearing aid may have a membrane 102 that may allow air conduction and/or bone conduction. In some embodiments, the membrane may be formed of a flexible, elastic, and/or stretchable material. In some embodiments, the membrane may be formed of a balloon. In some embodiments, the membrane may be fluid tight and may contain a fluid therein (such as air, other gas, gel, or a liquid). In other embodiments, the membrane is not fluid tight and air may be able to flow therein.

The membrane may permit dampening of vibration or sound. In some embodiments, there may be reduced sound transmission. Portions of the hearing aid may be sound absorbing or may act as a sound reflector. This may allow the hearing aid to avoid undesirable feedback. Preferably, there may be no or little feedback conduction of sound in the membrane. The hearing aid may contain the sound so that it does not echo through the ear canal. This may occur, even for high amplification.

The hearing aid may have a lateral area. The lateral area of the hearing aid may be greater at some cross-sections of the hearing aid. In some embodiments, the lateral area of some cross sections may be large enough to allow the hearing aid to contact a portion of the ear canal surface. In some embodiments, at least some cross sections may have lateral areas that a sufficiently small or shaped to not contact the ear canal surface. For example, the hearing aid may have a portion 104 that does not come into contact with the ear canal surface.

A hearing aid that may use a flexible part that may act as a passive sound amplifier, and/or may be used as an interface with the ear canal and/or the eardrum. The interface may allow the conduction of sound via air transmission and/or bone conduction. The interface may or may not come in contact with the eardrum and/or ear canal. The interface between the eardrum and the hearing aid may be used to conduct sound from the hearing aid to the eardrum. This interface may allow transmission of sound from the hearing aid to the eardrum to be established via air transmission or fluid transmission. The hearing aid may fit in its entirety inside the external ear canal, while preserving an open ear canal. The hearing aid may be secured inside the external ear canal using a compressible means that may be permeable to air, to maintain an open ear canal. In one embodiment, this securing mean may consist of a bunch of flexible bristles assembled in a shape that may look like a minuscule circular hair brush.

Figure 2A:
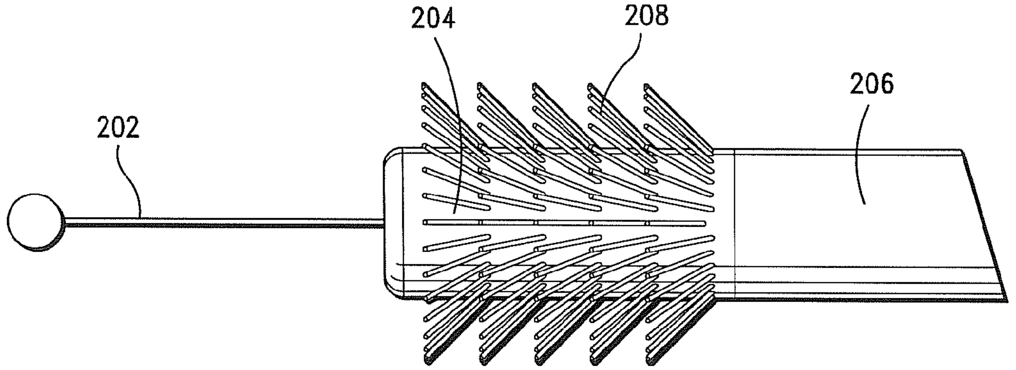
FIG. 2A shows an example of an open ear canal hearing aid in accordance with an embodiment the invention.

FIG. 2A shows an example of an open ear canal hearing aid in accordance with an embodiment the invention. The hearing aid may comprise a part to introduce or remove the hearing aid 202. The hearing aid may also include a part 204 that may contain electronic components. The hearing aid may also include a passive amplifier 206. In some embodiments, the hearing aid may include an additional part 208 that may secure the hearing aid inside the external ear canal.

One or more of the parts described may be integrated into one component or integrally connected. For example, a part may both contain electronic components and passively amplify signals. In another example, a securing part may be integrally formed on a part that contains electronic components. An electronics containing portion and a passive amplifier may be connected to one another. They may be connected as an integral piece or separate portions.

A part to introduce and remove the hearing aid 202 may be provided. In some embodiments, the introduction/removal portion of the hearing aid may be an extension or protrusion that a user may grasp. For example, the introduction/removal portion may have a wire-like form that may protrude from the rest of the hearing aid. The introduction/removal portion may be formed of a wire, any metal, plastic, silicone, rubber, resin, or any other material. The introduction/removal portion may have a smaller cross-sectional area than the ear canal. This may allow a user to reach within a user's ear canal and grasp the introduction/removal portion. In some embodiments, the introduction/removal portion may be within an ear canal when the hearing aid is in use. In other embodiments, the introduction/removal portion may protrude partway or wholly from the ear canal. The introduction/removal portion may be rigid, semi-rigid, or flexible. The introduction/removal portion may be an integral part of the rest of the hearing aid or may be separately formed and/or separable.

The introduction/removal portion may host a microphone at the outer end. In some embodiments, the outer end may be the end closest to the pinna, or outer ear. Positioning the microphone at the end of the introduction/removal portion may prevent, minimize, or reduce feedback, by creating a larger distance between the microphone and the portion used to transmit amplified sound to the ear, while keeping the ear canal open.

The hearing aid may include a part 204 that contains electronic components. The electronic component-containing portion may have a cylindrical shape. The shape may be roughly or substantially cylindrical. In other embodiments, the electronics-containing potion may have a prismatic shape. The cross-sectional area of the electronics-containing portion may have a circular shape, elliptical shape, any polygonal shape, or regular or irregular shape.

Some examples of electronic components that may be contained within a hearing aid may include a microphone, a battery, a sound processor, and/or an actuator. The battery or any other energy storage system may provide power to the other electronic components. The microphone may receive and/or collect sound. The sound processor may be used for sound amplification. The actuator may be used for sound transmission to a passive amplifier 206.

A passive amplifier 206 of the hearing aid may or may not come in contact with the eardrum and/or the ear canal. In one embodiment, the passive amplifier 206 may or may not be soft and cylindrical. The passive amplifier may be roughly or substantially cylindrical. The passive amplifier may be made of a flexible, elastic, and/or stretchable material. In some embodiments, the passive amplifier may be formed of a polymer, silicone, resin, rubber, elastomer, latex, polyurethane, polyamide, polyimide, nylon, or any other elastic or flexible material. The passive amplifier may have a flat end, curved end, or a tapered end. The end of the passive amplifier may or may not be configured to contact an ear drum.

The passive amplifier 206 may be used to transmit sound between the rest of the hearing aid and the eardrum using air transmission and/or other fluid transmission. The passive amplifier may also allow for sound transmission via bone conduction.

The passive amplifier 206 may create a closed channel between the hearing aid and the eardrum while maintaining an open ear canal. In one embodiment, the passive amplifier may consist of a closed envelope that may be filled with different materials such as but not limited to fluids such as a liquid, a gel, or a gas. The closed envelope may have a closed end. A fluid, such as a liquid, gel, or gas may be contained within the closed envelope. The fluid may be at various pressures. For example, the fluid may be at ambient air pressure, greater than ambient air pressure, or less than ambient air pressure. The fluids may be of various viscosities. Such materials may be used as sound amplifiers and/or filters.

In another embodiment, the passive amplifier 206 may consist of a tubular structure with an open end. The open end may be applied against the eardrum such as to create a seal between the passive amplifier and the eardrum. The passive amplifier may be elastically deformable along the longitudinal axis to facilitate a sustained, atraumatic, contact between the hearing aid and the eardrum. The passive amplifier may be an open tube. In some embodiments, when the open end forms a seal with the ear drum, fluid, such as air, may be trapped within the passive amplifier.

The distal end of the passive amplifier 206 may be applied against the eardrum. In some embodiments, the distal end may be applied directly, thereby allowing the distal end to directly contact the eardrum. In some other embodiments, an intermediate layer may be provided between the distal end and the eardrum. In one example, the intermediate layer may be a layer of material, such as, but not limited to, pomade or a gel. The layer of material may be applied between the distal end and the eardrum to improve the contact.

The hearing aid may include a part 208 that may secure the hearing aid inside the external ear canal. The securing mechanism may secure part or all of the hearing aid inside the ear canal. The securing mechanism may also be used to maintain the passive amplifier 206 at a desired location or orientation. For example, the securing mechanism may keep the passive amplifier in contact with the eardrum. In another example, the securing mechanism may keep the passive amplifier at a desired distance from the eardrum. In preferable embodiments, the securing part may keep the ear canal open and allow for comfortable extended wear.

The securing mechanism 208 may comprise a compressible or flexible portion that may be permeable to air, to secure part or all of a hearing aid while maintaining the ear canal open. The securing mechanism may have one or more air channel through the securing mechanism, or may allow one or more air channels to exist between the securing mechanism and the ear canal when the hearing aid is in use. One or more air flow paths may be provided through the hearing aid or between the hearing aid and ear canal surface. One or more air flow paths may provide fluid communication between one side of the hearing aid and an opposing side of the hearing aid. The opposing sides of the hearing aid may be on opposite longitudinal sides of the hearing aid (toward ear drum and away from ear drum) or on opposing lateral sides of the hearing aid.

In one embodiment, the securing mechanism 208 may include a bunch of small, soft, flexible bristles. The flexible bristles may be attached to a part of the hearing aid and, in some embodiments, may be assembled in a shape that may look like a circular hair brush. The securing mechanism may be attached to the electronics-containing part 204 of the hearing aid only, the passive amplifier 206 only, or both the electronics-containing part and the passive amplifier. The securing mechanism may be integrally formed on the electronics containing portion and/or the passive amplifier, or may be a separate or separable piece. The securing mechanism may extend from the electronics-containing part and/or the passive amplifier at a desired amount. The securing mechanism may contact a surface of the ear canal. For example, a plurality of flexible bristles may contact a surface of an ear canal when the hearing aid is in use. In some embodiments, the securing mechanism may contact the ear canal surrounding the hearing aid at one or more point. For example, if an axis is defined lengthwise along the hearing aid, the securing mechanism may be provided and/or may contact the ear canal surface at any angle around the lengthwise axis. In some embodiments, the securing mechanism may contact the ear canal at 360 degrees around the axis. Various possible configurations for the securing mechanisms are discussed in greater detail below. Any securing mechanism embodiment described elsewhere herein may be utilized.

Figure 2B:
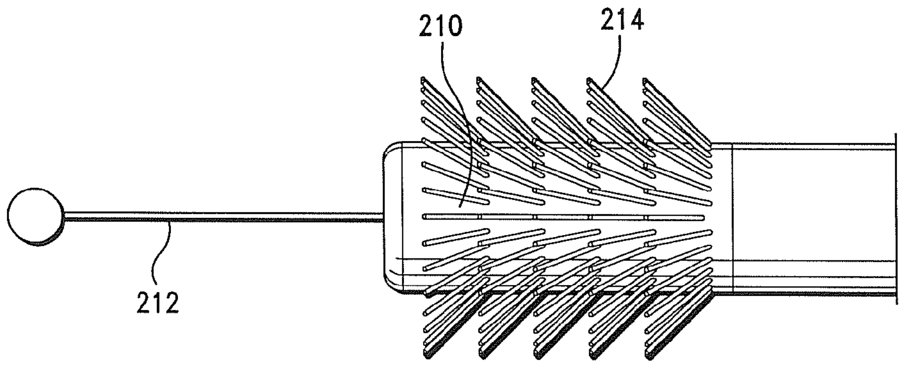
FIG. 2B shows another example of an open ear canal hearing aid.

As previously mentioned, in some embodiments, feedback may be prevented by mounting the microphone on a long proximal part of the hearing aid that may also be used to facilitate insertion or removal of the hearing aid inside the ear canal. FIG. 2B shows another example of an open ear canal hearing aid. The hearing aid may include an electronics containing portion 210, an elongated segment 212, and a securing mechanism 214.

The hearing aid may fit in its entirety inside the external ear canal, while preserving an open ear canal. The hearing aid may be secured inside the external ear canal using a compressible means that may be permeable to air, to maintain an open ear canal. In one embodiment, this securing mean may consist of a bunch of flexible bristles assembled in a shape that may look like a minuscule circular hair brush. The hearing aid may incorporate features described in other embodiments described herein.

A electronics containing portion 210 may contain electronic components, such as a battery, a sound processor, and an actuator. The sound processor may be used for sound amplification. The actuator may be used for sound transmission to an elongated segment 212. The electronics containing portion may be cylindrical. In some embodiments, the electronics containing portion may be a main body or part of a main body of the hearing aid.

A hearing aid may include an elongated segment 212 with a microphone at the end opposite to the electronics containing portion 210. In another embodiment, the microphone may be inside part (A) and part (B) may consist of an elongated sound conduction channel, such as a tube. Part (B) may also be used to facilitate insertion or removal of the hearing aid inside the ear canal.

A securing mechanism 214 may secure the hearing aid inside the external ear canal. The securing mechanism may also be used to maintain the electronics containing portion in contact with the eardrum.

In some embodiments, the securing mechanism 214 may have a bunch of small, soft, flexible bristles attached to the electronics containing portion 210 only, the elongated segment 212 only, or both the electronics containing portion and the elongated segment. The force applied by the securing mechanism to the ear canal may be tuned, for instance by varying the number of bristles, the size and shape of the bristles, and the angulations of the bristles with respect to the hearing aid and the ear canal. The cross-section of the bristles may have various shapes, such as but not limited to round or flat. The layout of the bristles of the securing mechanism on the electronics containing portion and/or the elongated segment may vary. For instance, the bristles may be laid out in a spiral shape, or in a series of circular disks, or in a random manner. The pressure exerted by the electronics containing portion against the eardrum may be tuned by varying the design of the securing mechanism. Such pressure against the eardrum may be adjusted, for instance by varying the number of bristles, the size and shape of the bristles, and the angulations of the bristles with respect to the hearing aid and the ear canal. Any other securing mechanism embodiment described elsewhere herein may be utilized.

A hearing aid may include or may not include a passive amplifier.

Figure 3:
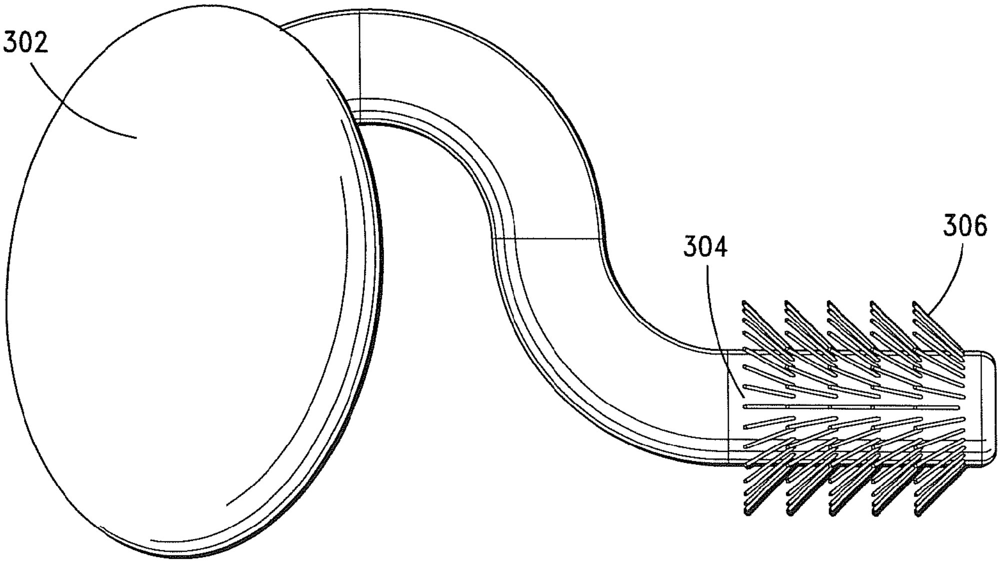
FIG. 3 shows an additional example of a hearing aid with a securing mechanism in accordance with an embodiment of the invention.

FIG. 3 shows an additional example of a hearing aid with a securing mechanism in accordance with an embodiment of the invention. The hearing aid may have an electronic component-containing part 302, a conduit 304, and a securing mechanism 306. In some embodiments, the conduit may function as a passive amplifier. The securing mechanism may include bristles, balloons, and/or may have other configurations described elsewhere herein.

In some embodiments, the electronic component-containing part may be provided external to the ear canal while in other embodiments, it may be provided within the ear canal. The hearing aid may be a behind-the-ear (BTE) hearing aid, an in-the-canal hearing aid, or a completely-in-the-canal hearing aid. The conduit may be provided within the ear canal. In some embodiments, a portion of the conduit may be provided external to the ear canal, while in other embodiments, the conduit may be entirely within the ear canal. Preferably, the securing mechanism may contact a portion of the ear canal surface.

The conduit may be formed of a flexible material. In some embodiments, the conduit may be formed of a cylinder. The conduit may be roughly or substantially cylindrical. The cylinder may be straight. In other embodiments, the cylinder may be soft and flexible, and may bend. In some embodiments, the conduit may have a naturally bent shape. The conduit may be closed or open. If the conduit is closed, it may contain a fluid therein, such as a gas, liquid, or gel.

The position of the securing mechanism, which may be a bristle assembly, may be within the bony inner portion of the ear canal or the outer cartilaginous portion. If it is placed in a medial portion, it may be medial to the hair follicles and or sweat, cerumen, and/or other glands. This may allow the hearing aid components to not trap any materials secreted by the user medial to the hearing aid components. This may also allow for improved wax and material removal when the hearing aid materials are removed. Being located medial to the hair follicles allows for improved contact with the ear canal surface. This can allow for a better hold. It can also allow for improved auditory bone conduction. The hearing aid components may include bristles, bristle assembly, or the AquaSound component, or a combination of the two.

The force applied by the securing mechanism to the ear canal may be tuned, for instance by varying the number of bristles, the size and shape of the bristles, the bristle material, and the angulations of the bristles with respect to the hearing aid and the ear canal. The cross-section of the bristles may have various shapes, such as but not limited to round or flat bristles.

The layout of the bristles of the securing mechanism on the electronic components-containing part and/or the passive amplifier may vary. For instance, the bristles may be laid out in a spiral shape, in a series of circular disks, as rows extending lengthwise along the hearing aid, as zig-zags, as an even covering, as an array, or in a random manner. In some embodiments, the configuration of the bristles of the securing mechanism may be the same for the electronics-containing part and the passive amplifier. In other embodiments, the bristle configuration may vary between the electronics-containing part and the passive amplifier, or along any other portions or divisions of the hearing aid.

The pressure exerted by the passive amplifier against the eardrum may be tuned by varying the design of the securing mechanism. Such pressure against the eardrum may be adjusted, for instance by varying the number of bristles, the size and shape of the bristles, and the angulations of the bristles with respect to the hearing aid and the ear canal.

Figure 4A:
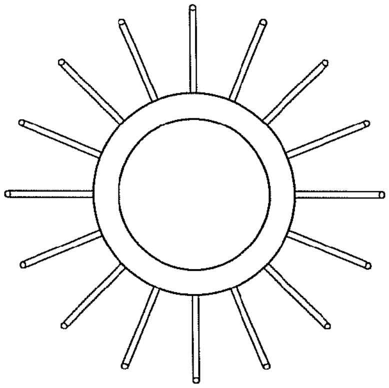
FIGS. 4A-4C show cross sections of various hearing aid securing mechanisms with different degrees of bristles.
Figure 4B:
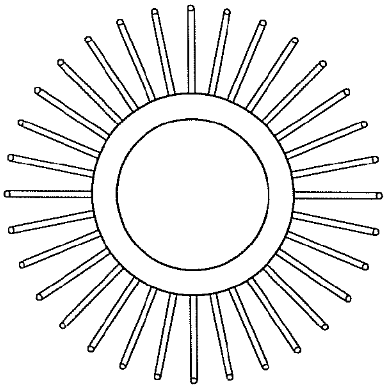
Figure 4C:
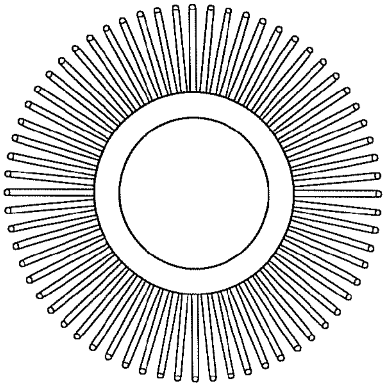

FIGS. 4A-4C show cross sections of various hearing aid securing mechanisms with different degrees of bristles. For example, FIG. 4A shows a more open configuration with fewer bristles. FIG. 4B shows a more closed configuration with a greater number of bristles. FIG. 4C shows an even more closed configuration with an even greater number of bristles. The larger the number of bristles, the more stiffly or strongly the hearing aid may be secured within the ear canal, due to the larger number of contact points between the hearing aid and ear canal surface. If a large number of relatively evenly distributed bristles are used, a large number of relatively evenly distributed contact points between the hearing aid and the ear canal may be provided. The fewer the number of bristles, the more loosely, but flexibly, the hearing aid may be secured within the ear canal. Fewer bristles may be more forgiving to oddly shaped ear canals or shaped features therein. In some embodiments, the bristles may flex or bend to accommodate the shape of the ear canal.

Any density of bristles may be provided on a hearing aid. For example, 1 or more, 5 or more, 10 or more, 15 or more, 20 or more, 25 or more, 30 or more, 50 or more, 75 or more, 100 or more, 125 or more, 150 or more, 200 or more, 250 or more, 300 or more, 400 or more, 500 or more, 700 or more, 1000 or more, 2000 or more, 3000 or more, 4000 or more, 5000 or more, 7000 or more, or 10,000 or more bristles per square centimeter may be provided. The bristles may have the same length or may have varying lengths. For example, bristles may have lengths greater than, less than, or falling between any of the following: 0.1 mm, 0.2 mm, 0.3 mm, 0.4 mm, 0.5 mm, 0.7 mm, 1 mm, 1.5 mm, 2 mm, 2.5 mm, 3 mm, 3.5 mm, 4 mm, 4.5 mm, 5 mm, 5.5 mm, 6 mm, 7 mm, 8 mm, 9 mm, 1 cm, 1.1 cm, 1.2 cm, 1.3 cm, 1.5 cm, 1.7 cm, 2 cm, 2.5 cm, or 3 cm.

The bristles may have any cross sectional shape or size. For example, the bristles may be flat, rounded, elliptical, square, triangular, hexagonal, or have any other cross sectional shape. The bristle may have a diameter, length, or width, greater than, less than, or falling between any of the following, 1 μm, 2 μm, 3 μm, 5 μm, 7 μm, 10 μm, 15 μm, 20 μm, 30 μm, 50 μm, 75 μm, 100 μm, 125 μm, 150 μm, 200 μm, 300 μm, 500 μm, 1 mm, 2 mm or 3 mm.

The use of a hearing aid as described herein may provide advantages over existing hearing aids. For example, the open canal hearing aid may be fully inserted inside the ear canal and is not visible from the outside. The securing mechanisms provided for the hearing aid may prove to be more comfortable than traditional hearing aid-fixing assemblies, especially the shape of the cross-section of the ear canal is being altered by movements of the lower jaw, such as during chewing or talking. The hearing aid utilizing bristles or other securing mechanisms described elsewhere herein may be a "one size fits all" and conform to a broad range of ear canal anatomies. The hearing aid may have a low profile that may make it easy to introduce inside the ear canal.

The hearing aid as provided in accordance with embodiments of the invention may reduce or prevent Larsen effects or other types of feedback. This may allow for higher amplifying levels. There may be little energy loss over the process of sound transmission, which may result in a very efficient system.

The hearing aid may preserve an open ear canal. The ear canal is not clogged or fully occluded by the hearing aid. Most traditional in-ear hearing aids plug the ear canal, which may be uncomfortable and painful. The hearing aid described herein may be prove substantially more comfortable and allow for longer wear time. It may maintain air circulation within the ear canal. Furthermore, the level of occlusion of the ear canal by the securing mechanism may be adjusted, for instance by varying the number of bristles.

In some embodiments, the hearing aid may allow to be transmitted via air transmission and bone conduction. Because sound may be transmitted by both ways, with or without direct contact with the malleus bone or the external ear canal, the current invention may be suitable for patients who suffer perceptive deafness and/or transmission deafness. This invention may also be suitable for patients suffering from cophotic deafness and may allow for pseudo-stereophony via bone conduction. The open canal hearing aid may allow for bone conduction without applying significant pressure on the mastoid bones, which may be painful and/or uncomfortable. The open canal hearing aid may achieve bone conduction without the need for implanting anchors in the bones.

The hearing aid may take advantage of the filter effect of the passive amplifier. The choice of the filling fluid (if any), the choice of material for the passive amplifier (e.g., envelope/balloon), and the choice of pressure of the passive amplifier may create a passive amplifier that will preferentially amplify a preferred range of frequencies, such as higher frequencies. This passive filter may also be adjusted to dampen unwanted frequencies. Some surfaces on the hearing aid may also contact features, shapes, and textures and may be compliant or spongy so as to scatter or absorb sound. This may be useful for instance to block sound from the speaker from reaching the microphone.

The hearing aid as provided in accordance with embodiments of the invention may be well suited for age-related deafness by preferentially and/or selectively facilitating transmission of higher-frequency sounds. Indeed, most age-related deafness may affect preferentially the hearing of higher-frequency sounds. The choice of the filling fluid, the choice of material for the passive amplifier, and the choice of pressure of the amplifier may allow to create a passive amplifier that will preferentially amplify higher frequencies.

The hearing aid may preserve the physiological hearing process, in the sense that the amplifying process takes place very close to the eardrum. By providing a passive amplifier that may or may not contact the ear drum, the amplification process may occur close to the eardrum. This may prevent unwanted sound interference.

The hearing aid as described herein may be waterproof and worn in many situations, such as during swimming. The hearing aid may also be worn during sleep without discomfort. This may allow the hearing aid to be utilized during many times when traditional hearing aids may provide discomfort or not work.

The bristles described in one embodiment of the present invention may clean the ear canal every time the present invention is removed from the ear canal. The hearing aid design may also prevent the accumulation of earwax during its insertion into the ear canal, due to its low profile and open design. The flexibility of the bristles may prevent ear wax from being pushed into the ear canal when the hearing aid is inserted.

Figure 5:
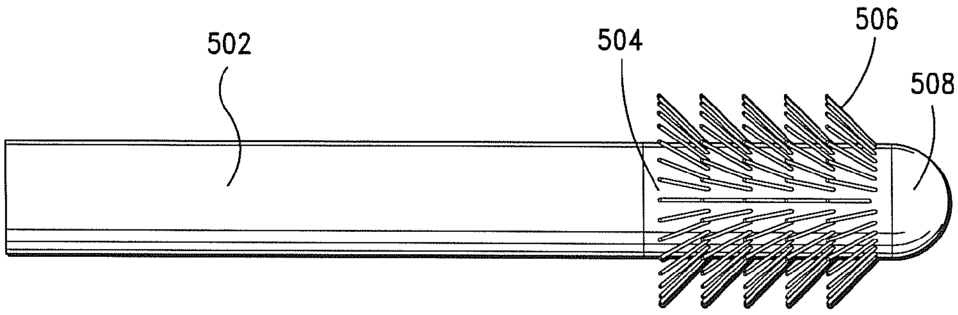
FIG. 5 shows an example of an ear cleaning mechanism.

FIG. 5 shows an example of an ear cleaning mechanism. The ear cleaning mechanism may be a cleaning brush. The cleaning brush may include a handle 502, cleaning area 504 with flexible bristles 506, and an inner tip 508. The handle and tip may be at opposing sides from the cleaning area.

The handle 502 may be made of various materials of various flexibilities. The handle may be rigid, semi-rigid, or flexible. The handle may be solid or hollow. The handle may or may not contain other components therein, such as electronic components. In some embodiments, a portion of a handle may contain a fluid therein. In one embodiment, the handle may be a plastic stick.

The cleaning area 504 may comprise flexible bristles 506. The cleaning effect may be adjusted by varying the dimensions of the bristles, the inclination of the bristles with respect to the ear canal, and more. The cross-section of the bristles may have various shapes, such as but not limited to round, oval or flat. The layout of the bristles may vary. For instance, the bristles may be laid out in a spiral shape, or in a series of circular disks, in a random manner, or any other configuration discussed elsewhere. The bristles may have any configuration as discussed elsewhere herein, relating to a hearing aid securing mechanism.

The inner tip 508 may be soft and atraumatic. The inner tip may or may not be part of the cleaning area. The inner tip may or may not be covered with bristles. In some embodiments, the inner tip may be rounded. The inner tip may be formed of a flexible or elastic material. The inner tip may be integrally formed on the cleaning area, or may be a separable component to the cleaning area.

Advantages may be provided by using the ear cleaning mechanism. The introduction of the cleaning brush inside the ear canal may be easy and atraumatic. This cleaning brush may allow for efficient and atraumatic cleaning of the ear canal at each removal of the brush. This cleaning brush may currently be a tool that allows for truly and efficiently performing self-cleaning of the ear canal (cleaning of user's ear canals by user).

In accordance with some embodiments, of the invention, the ear cleaning mechanism may be provided as part of a hearing aid as described previously. For example, the handle of the ear cleaning mechanism may incorporate a hearing aid introduction or removal part, an electronics containing part, and/or passive amplifier or vice versa. The cleaning area of the ear cleaning mechanism may incorporate a passive amplifier and/or electronics-containing part or vice versa. The bristles of a cleaning brush may incorporate the securing mechanism of a hearing aid or vice versa. Thus, an ear cleaning brush may be used as a hearing aid and may incorporate components of a hearing aid. Similarly, a hearing aid with bristles or other securing mechanisms may be used as an ear cleaning brush.

Figure 6:
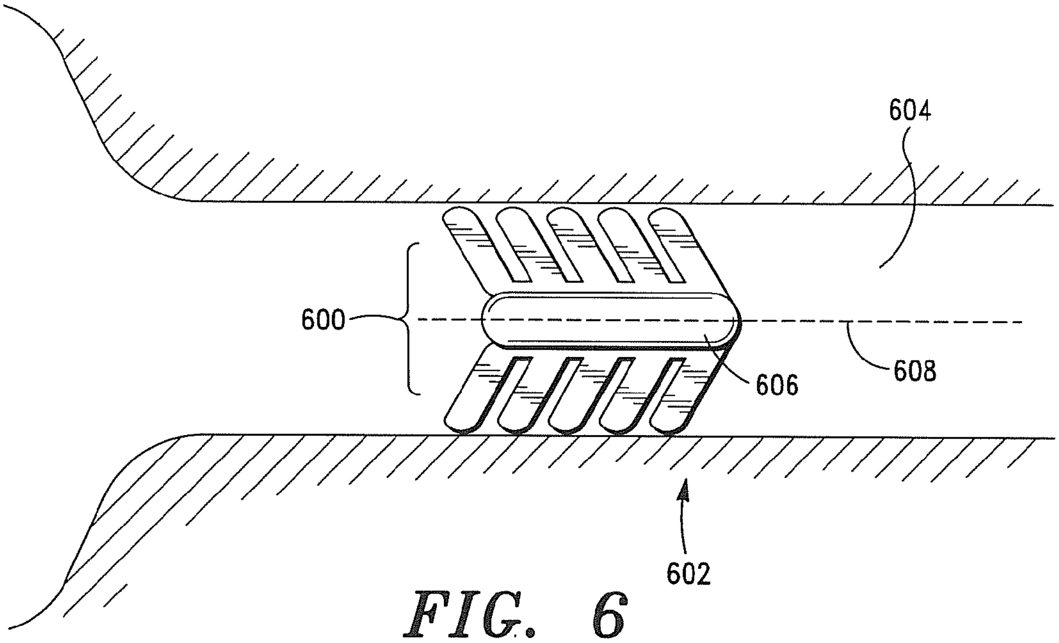
FIG. 6 shows an example of a hearing aid with a bristle assembly within an ear canal.

FIG. 6 shows an example of a hearing aid 600 with a bristle assembly 602 within an ear canal 604. In some embodiments, the hearing aid may be entirely within the ear canal. The hearing aid may have a central body 606 from which the bristle assembly may extend. The central body is not required to contact the ear canal surface. In some embodiments, the central body may include one or more electronic components therein, such as the electronic components previously described.

The bristle assembly 602 may extend from the central body 606 and may contact the ear canal 604 surface. This may allow air circulation between the ear canal surface and the central body of the hearing aid, between the bristles. This may keep a relatively open ear canal while the hearing aid is in use.

In some embodiments, an axis 608 may be provided lengthwise along the hearing aid. In some embodiments, the bristles may be provided at an angle to the lengthwise axis. For example, the bristles may be perpendicular to the lengthwise axis. Alternatively, the bristles may have any other angle to the lengthwise axis, including, but not limited to about 5 degrees, 10 degrees, 15 degrees, 20 degrees, 30 degrees, 40 degrees, 45 degrees, 50 degrees, 60 degrees, 70 degrees, 75 degrees, 80 degrees, or 85 degrees.

In some embodiments, the bristles may be angled so that the free ends of the bristles are directed toward the exterior of the ear canal (outside the ear). This may advantageously allow hearing aid to be easily pushed into the ear canal. This may also allow the bristles to collect ear wax and clean the ear when the hearing aid is removed from the ear canal. In some embodiments, the bristles may be angled so that the free ends of the bristles are directed toward the interior of the ear canal (toward the eardrum).

Figure 7:
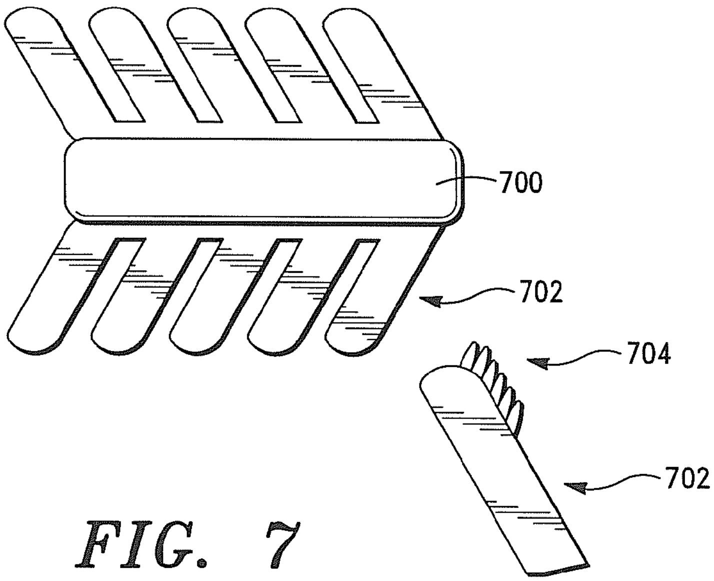
FIG. 7 shows an example of a hearing aid with major and minor bristles.

In another variant, the bristles previously discussed (major bristles) may also have finer bristles (minor bristles) on their surfaces. FIG. 7 shows an example of a hearing aid with major bristles 702 and minor bristles 704. The minor bristles may be attached to a surface of the major bristles.

The minor bristles 704 may extend on part or all of the major bristles 702. They may cover partway along the length of the major bristles and they may cover partway around the major bristles. For example, the minor bristles may cover the entire length of the major bristles, or part of the length of the major bristles. In some instances, the minor bristles may be closer to the free end of the major bristles. In other instances, the minor bristles may be closer to the end of the major bristle that is attached to a central body 700 of the hearing aid. The minor bristles may go entirely around the major bristles. Alternatively, they may go partway around the major bristles, or may be provided at certain intervals along the major bristles. The minor bristles may be provided toward an outer portion of a major bristle (toward an ear canal surface) or toward an inner portion of a major bristle (toward the hearing aid central body). The minor bristles may be distributed in the same manner for each major bristle or may vary from major bristle to major bristle.

Figure 8:
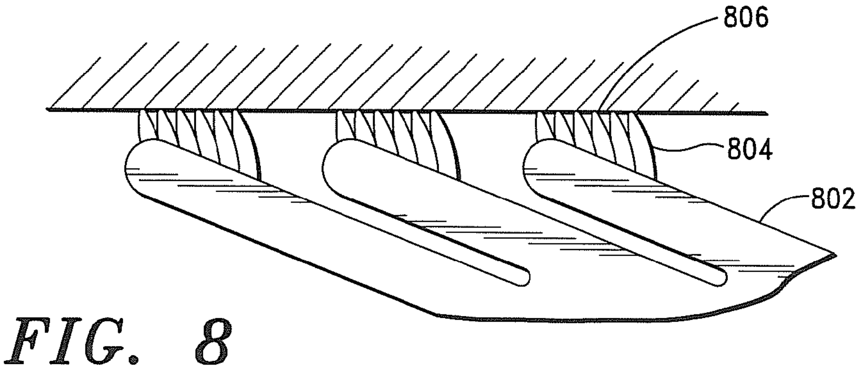
FIG. 8 shows an example of major and minor bristles of a hearing aid contacting an ear canal surface.

FIG. 8 shows an example of major 802 and minor bristles 804 of a hearing aid contacting an ear canal surface 806. In one embodiment, the minor bristles cover the outer portions of the major bristles that come in contact with the ear canal. These minor bristles may take the form of small buds, hairs, filaments, hook-like structures, ridges, or other protrusions. The minor bristles may be sufficiently small so as to allow for sufficient adhesion via Van der Waals forces to the surface of the ear canal. The minor bristles may assist with keeping the hearing aid in position within the ear canal, and prevent the hearing aid from slipping.

The major and minor bristles may be made of the same or different materials. Some materials include silicone, rubber, resin, elastomer, latex, polyurethane, polyamide, polyimide, nylon, or other materials that are compliant and flexible. Within each type of material used, the composition, density, softness, and other properties may be varied within any given bristle, between bristles, or between minor and major bristles. In one embodiment the minor and major bristles are both made of silicone with the minor bristles being made of silicone that is softer than the major bristles. In another variation, the major bristle becomes softer along the length of the bristle such that the tip and/or more external portions are softer. In some embodiments, the minor bristles may have a shorter length than the major bristles. For example, they may be about 0.1%, 0.5%, 1%, 2%, 3%, 5%, 10%, 15%, 20%, 30%, or 50% of the length of the major bristles. Alternatively, they may have the same length or be longer than the major bristles.

In one variation, the bristle angle can be changed. In one such embodiment the bristles may be pulled flatter so as to make the bristle assembly thinner, thereby providing a collapsed configuration. The can allow for greater ease of insertion or removal. It may also allow for insertion of the bristle assembly with less ear wax and other materials being moved towards the back of the ear. The bristles can then be erected again upon removal of the bristle assembly to aid in removal of wax and other materials from the ear canal, thereby providing an open configuration.

Figures 9A, 9B:
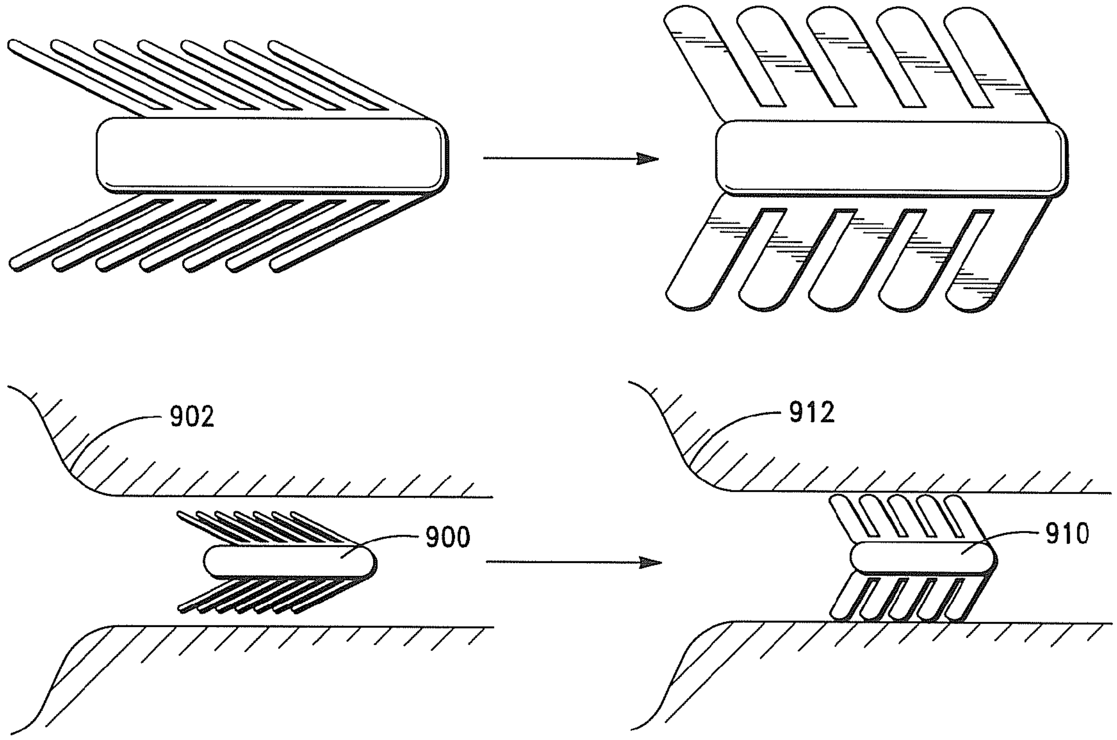
FIG. 9A shows an example of a hearing aid with bristles in a collapsed configuration.
FIG. 9B shows an example of a hearing aid with bristles in an open configuration.

FIG. 9A shows an example of a hearing aid with bristles in a collapsed configuration. When the bristles are collapsed, the hearing aid has an overall thinner profile. The bristles may have a smaller angle relative to a lengthwise axis of the hearing aid, than when the bristles are in an open configuration. For example, in some embodiments, the bristles may be at <x angle, where x may be 5, 10, 15, 20, 30, 40, 45, 50, 60, or 70 degrees.

When the hearing aid 900 is inserted into an ear canal 902, the hearing aid is not required to contact the ear canal surface. There may be space provided between the hearing aid and the ear canal surface. As previously mentioned, this may allow easy insertion. This may also prevent earwax from being pushed into the ear.

FIG. 9B shows an example of a hearing aid with bristles in an open configuration. In some embodiments, the bristles may be opened after the hearing aid is inserted into the ear with a collapsed configuration. When the bristles are opened, the hearing aid may have an overall thicker profile. The bristles may have a larger angle relative to a lengthwise axis of the hearing aid, than when the bristles are in a collapsed configuration. For example, in some embodiments, the bristles may be at <x angle, where x may be 10, 15, 20, 30, 40, 45, 50, 60, 70, 80, or 85 degrees.

After the hearing aid 910 as inserted into an ear canal 912, and the hearing aid has been opened, bristles of the hearing aid may contact the ear canal surface. In some embodiments, each of the bristles, or many of the bristles may contact the ear canal surface. There may be space provided between the hearing aid central body and the ear canal surface. This may keep the hearing aid securely in place.

In some embodiments, any discussion of adjusting bristle angle or configuration may apply to other securing mechanisms. An adjustable securing mechanism may be provided, which may be adjusted from a first position to a second position. In one example, the first position may be a collapsed configuration while the second position may be an expanded configuration. In another example, the first position may be an expanded configuration while the second position may be a collapsed configuration. In other embodiments, the adjustable securing mechanism may be adjusted to vary the size or volume of the securing mechanism. The adjustable securing mechanism may be adjusted to vary the profile of the securing mechanism.

In some embodiments, the hearing aid may be returned to a collapsed position before removing the hearing aid from the ear canal. This may allow the hearing aid to slide out for easy removal. In other embodiments, the hearing aid may remain in an open position, or may be in some intermediate position while the hearing aid is removed from the ear canal. This may allow bristles or other securing mechanisms to contact the side of the ear canal while the hearing aid is removed, thereby cleaning the ear canal.

Figure 10A:
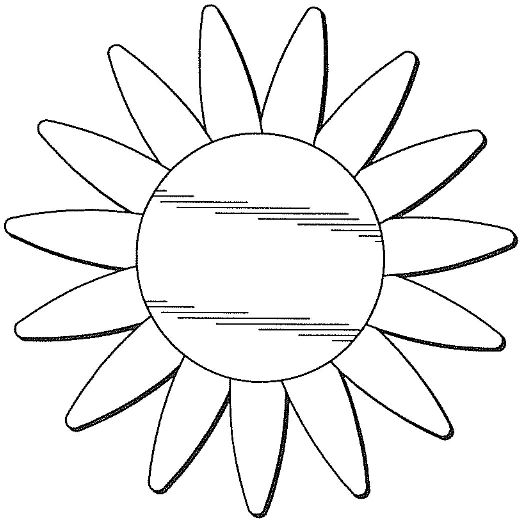
FIG. 10A shows a cross section of a hearing aid with bristles in an open configuration.
Figure 10B:
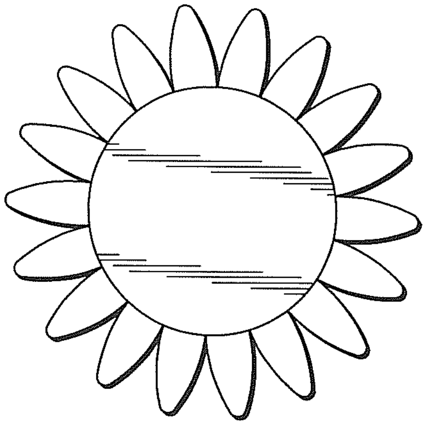
FIG. 10B shows a cross section of a hearing aid with bristles in a collapsed configuration.

FIG. 10A shows a cross section of a hearing aid with bristles in an open configuration. FIG. 10B shows a cross section of a hearing aid with bristles in a collapsed configuration. As previously mentioned, the collapsed configuration has a thinner profile. Thus, the cross-sectional area of the hearing aid with open bristles may be larger than the cross-sectional area of the hearing aid with collapsed bristles.

Figure 10C:
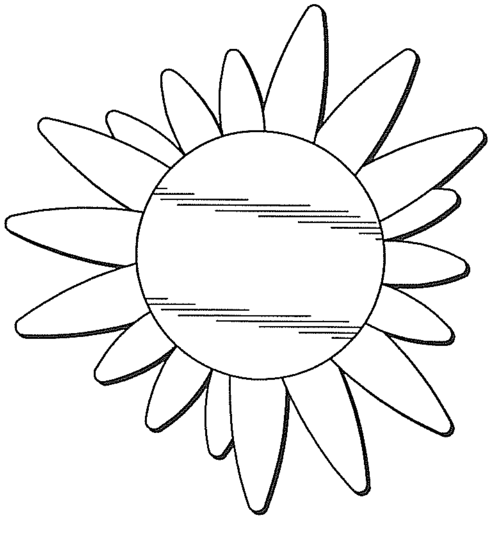
FIG. 10C shows a cross section of a hearing aid with some collapsed bristles and some open bristles.

FIG. 10C shows a cross section of a hearing aid with some collapsed bristles and some open bristles. In some embodiments, only some of the bristles may be opened and/or only some of the bristles may be collapsed. In some embodiments, individual sections of the bristles may be independently controllable. The individual sections may be independently collapsed and/or opened. In some embodiments, the individual sections may be provided at different locations around the hearing aid. For example, three collapsed sections and three open sections may be provided around the hearing aid. In some embodiments, the independent sections may be evenly or unevenly spaced from one another. Alternatively, the individual sections may be provided at different locations along the length of the hearing aid.

The bristles may have any intermediate state of being opened or collapsed. The angle of a bristle may be adjusted by any degree. For example, a bristle may be opened or closed about 1 degree, 5 degrees, 10 degrees, 15 degrees, 20 degrees, 25 degrees, 30 degrees, 40 degrees, 45 degrees, 50 degrees, 60 degrees, 70 degrees, or 80 degrees.

The bristles can be adjusted on the bristle assembly in several ways. A force may be exerted to a bristle to adjust the angle of the bristle. For example, a force may be exerted to an end of a bristle that is attached to a central body of a hearing aid. In some embodiments, the force may be exerted from within the central body of the hearing to the end of the bristle. The force may be a pulling force or a pushing force. The force may be directed toward the side of the hearing aid closer to the ear drum, or the force may be directed toward the side of the hearing aid away from the ear drum. In another example, a force may be exerted to a portion of a bristle extending from the central body of the hearing aid.

One such way is by exerting a force on a string or rod attached to the bristle assembly. The string or rod may move relative to the bristle assembly and actuate a motion in the bristles. The string or rod may exert a force on an end of a bristle that is attached to a central body of the hearing aid. In some embodiments, the string or rod may directly contact the bristle end. Alternatively, the string or rod may contact additional components that may contact the bristle end or may extend into the interior of a bristle.

Figure 11A:
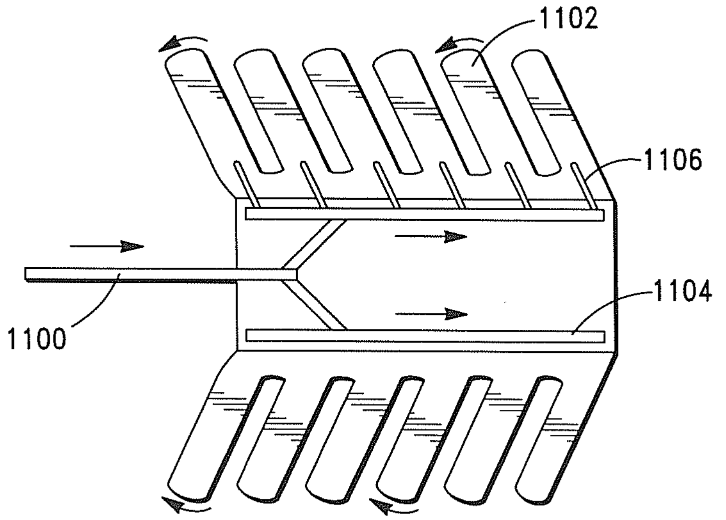
FIG. 11A shows an example of how to collapse bristles using a rod.

FIG. 11A shows an example of how to collapse bristles using a rod. Pushing a rod 1100 may cause bristles 1102 to collapse. The rod may be connected to an internal structure, such as a tube or internal rods 1104. Pushing the rod may cause the internal structure to move correspondingly. The internal structure may be connected to bristle actuators 1106. The bristle actuators may be provided with the bristles or connected to the bristles. The bristle actuators may have a pivot point so that when one end of a bristle actuator is moved, the other end of the bristle actuator may move in the opposite direction, thereby causing the bristle actuator to pivot about the pivot point. For example, if an end of a bristle actuator contacting the internal structure is moved when the internal structure is pushed, this may cause the bristles contacting the bristle actuator to collapse.

In some embodiments, the rod may be pulled to open the bristles. Pulling the rod may cause the internal structure to be pulled as well. The internal structure may contact bristle actuators that may pivot about a point, so that when the internal structure is pulled, the bristles may assume an open position.

Figure 11B:
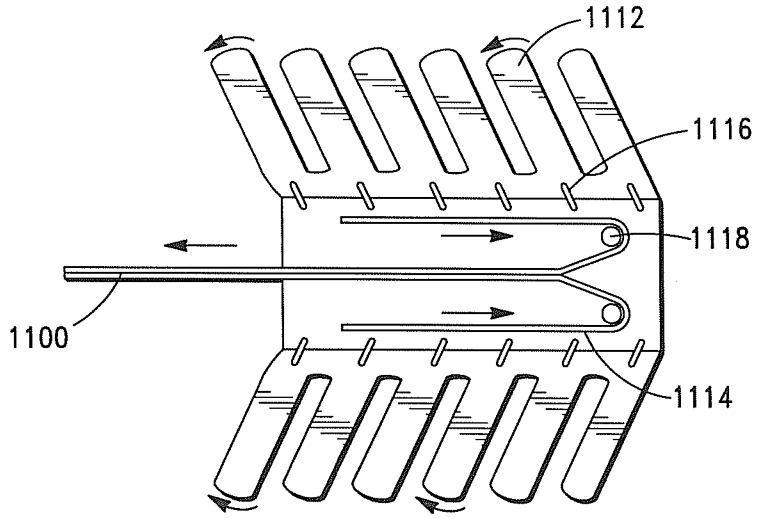
FIG. 11B shows an example of how to collapse bristles using a string.

FIG. 11B shows an example of how to collapse bristles using a string. Pulling a string 1110 may cause bristles 1112 to collapse. The string may be connected to an internal structure, such as a netting, mesh, or strings 1114. Pulling the string may cause the internal structure to move correspondingly. In some embodiments, a support 1118 may be provided so that when the string 1110 is pulled in a first direction, the internal structure 1114 moves in the opposite direction. The support may be a frame, bar, or ring. The internal structure may be connected to bristle actuators 1116. The bristle actuators may be provided with the bristles or connected to the bristles. The bristle actuators may have a pivot point so that when one end of a bristle actuator is moved, the other end of the bristle actuator may move in the opposite direction, thereby causing the bristle actuator to pivot about the pivot point. For example, if an end of a bristle actuator contacting the internal structure is moved when the internal structure is goes away from the pivot point, or toward the end of the hearing aid facing the ear drum, this may cause the bristles contacting the bristle actuator to collapse.

A pivot point may be provided anywhere along a bristle or bristle actuator. It may be at an end or middle of a bristle or bristle actuator. In one example, it may be where a bristle meets a central body of a hearing aid.

As previously mentioned, subsets of the bristles may be opened or collapsed. The independent sections may be connected to independent force providing mechanisms. For example, multiple rods connected to different bristles, or multiple strings connected to different bristles, or any combination thereof may be used to independently control the collapsing and opening of different sections of bristles. In some embodiments, only one rod or one string may be provided, but they may be connected to only some of the bristles. For example some of the bristles need not be collapsible or openable.

Figure 12:
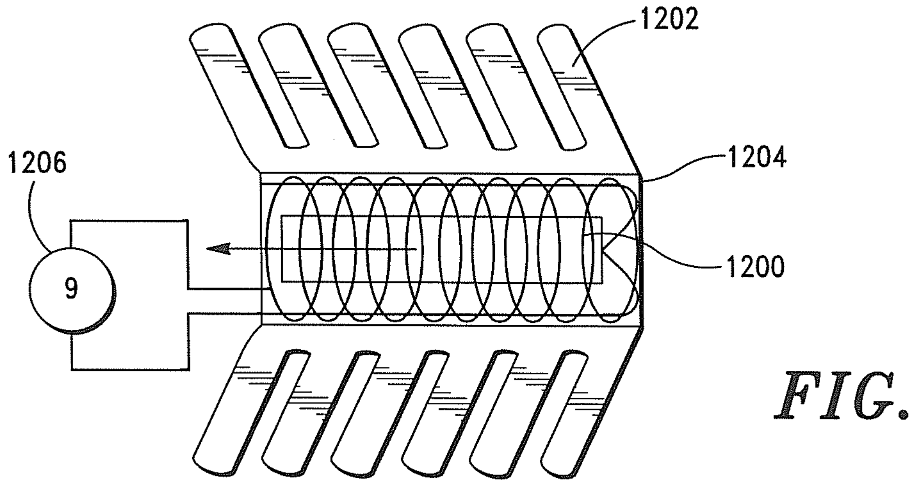
FIG. 12 shows an example of how to control bristle angles using currents.

Another method of adjusting a bristle assembly is via an electrical signal directed towards the bristle assembly. FIG. 12 shows an example of how to control bristle angles using currents. There may be a coil of wire 1200 that, when current is passed through, exerts a force on the bristles 1202 or a body 1204 that is attached to the bristles. In some embodiments, a current source 1206 may be provided. In some embodiments, the current source may be connected to a battery or energy storage system of the hearing aid. In some embodiments, a relationship may be provided between the amount of current and the angle of the bristle. For example, having a larger amount of current passing through may cause a greater degree of bristle collapse or bristle openness. A smaller amount of current passing through may cause a lesser degree of bristle collapse or bristle openness. In other embodiments, a voltage source may be provided instead of, or in addition to the current source. The bristles may respond to the amount of current, voltage, or any other electrical signal or characteristic.

In moving the bristles, some or all of the bristles may move. More than one actuator can be used to adjust the position of different sets of bristles or allow for different types of motion. The bristles may also move with different signals from the hearing aid. The bristle angles may adjust based on signals automatically received from the hearing aid. The bristle angles may be adjusted based on manual adjustments by a user.

There can be periodic or planned movement of the bristles, or subsets of the bristles, during normal use of the hearing aid to allow for relief of pressure on the ear canal. For example, the hearing aid may include a processor and/or memory that may store regimens for bristle movement. Tangible computer readable media may provide code, logic, or instructions for performing any steps or algorithms described herein. In some embodiments, one or more clock may be provided that may assist with timing of bristle movements. Bristles may move in accordance to signals/instructions provided from the hearing aid. In some embodiments, one or more sensors may be provided that may take one or more measurement. In some embodiments, bristles may move depending on measurements taken. For example, if a temperature sensor detects that an ear canal surface is getting hot, some of the bristles may be collapsed to allow greater air circulation within the ear canal. As another example, some or all bristles may collapse periodically to allow for variation in the pressure exerted on the ear canal, thus allowing for improved blood circulation. If only a subset of the bristles move at any given time, the bristle assembly continues to exert sufficient force on the ear canal to remain in place.

Figure 13A:
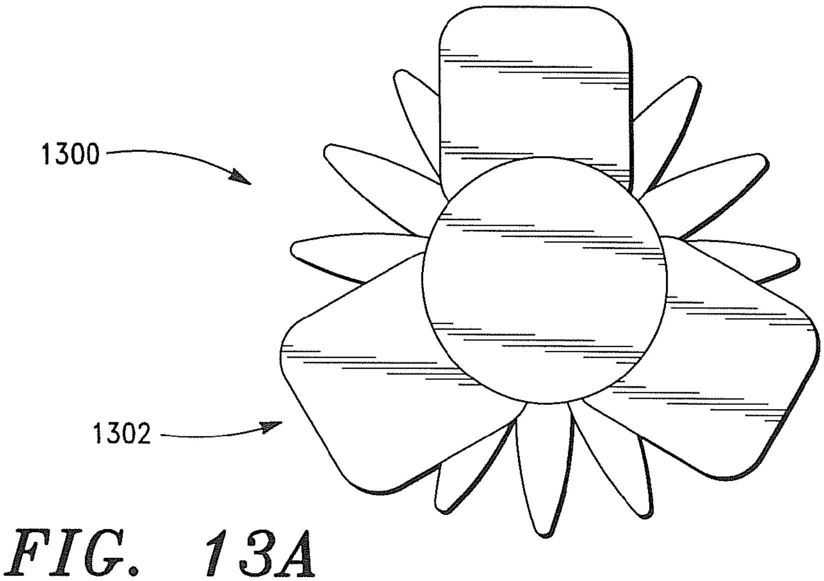
FIGS. 13A and 13B provide cross sections of a hearing aid with bristles and/or balloons.
Figure 13B:
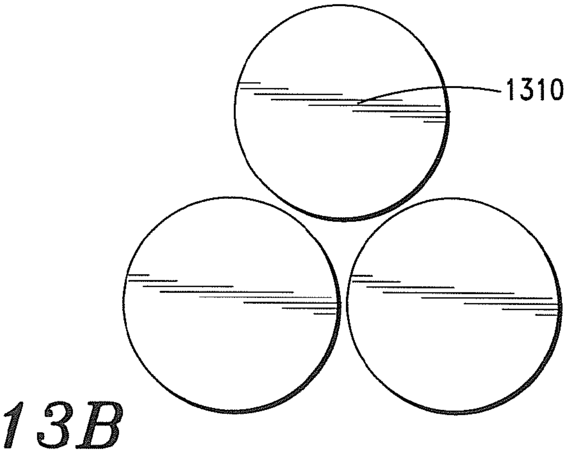

In some embodiments, a securing mechanism may utilize bristles and balloons. FIGS. 13A and 13B provide cross sections of a hearing aid with bristles and/or balloons. For example, one or more sections of bristles 1300 and one or more balloons 1302 may be provided on a central body 1304 of a hearing aid. In some embodiments, alternating bristles and balloons may be provided. This may allow the holding forces of the hearing aid to the ear canal to be distributed between bristles and balloons. In some embodiments, there may not need to be separate balloon and bristle segments. The overall configuration may be more compact.

In some embodiments, balloons of differing compliance, pressure, fluids, and densities may be used. In some embodiments, each of the balloons may vary, each of the balloons may be the same, or some of the balloons may vary. FIG. 13B also shows a cross section with multiple balloons 1310.

In some embodiments, balloons without bristles may be used as a securing mechanism for a hearing aid. Alternatively, any embodiment herein describing balloons may also include bristles. The bristles may have any configuration or actuation mechanism as described elsewhere herein. The balloons may enclose a fluid. The fluid may be a liquid, gel, or gas.

A fluid enclosed by a membrane (which may be formed by a balloon) that comes into contact with the user's ear canal or ear drum. The fluid may be a gas or a liquid. The fluid pressure, viscosity, composition, and density amongst other characteristics may vary. The membrane's compliance, thickness, and density amongst other characteristics may vary.

The pressure or volume of fluid within the balloons can be adjusted. The degree of inflation of one or more balloon may be adjustable. These characteristics can be adjusted and set once, or they can be adjusted several times in the component's life cycle. Some methods for adjusting the balloons include using a syringe-like injection device to add or remove fluid, potentially through a valve or membrane that can be punctured one or more times. The balloon assembly may have a maximum pressure (or maximum volume) release mechanism, such that no more fluid can be added or additional fluid escapes beyond a specified pressure or volume. This maximum pressure release system can be part of the injection device. The pressure or volume of the balloon(s) may also be varied during normal use or when being inserted or removed.

The pressure or volume can vary periodically, or based on signals from the hearing aid or other internal or external control device. The variation in pressure may be due to large amplitude movements in one or more actuators, for example the speaker, attached to the balloon. The variation in pressure of volume can also be accomplished by an opening or closing of a valve. These variations in pressure can be used to improve comfort, circulation, or to move the balloon or hearing aid assembly.

Figure 14A:
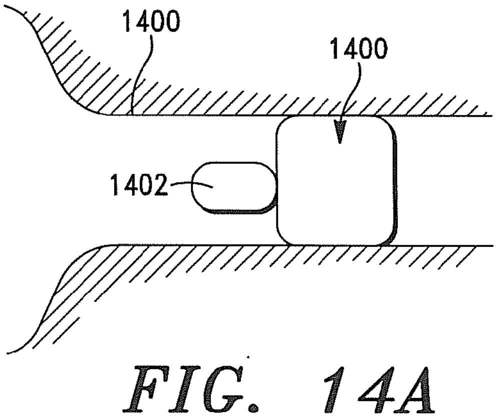
FIGS. 14A-14B provide examples of a hearing aid with a balloon configuration in an ear canal.
Figure 14B:
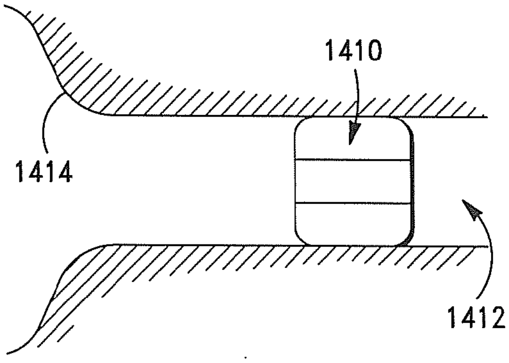

FIGS. 14A-14B provide examples of a hearing aid with a balloon configuration in an ear canal. In some embodiments, the hearing aid may have one or more balloon that secures the hearing aid in place within the ear canal. The balloon may contact the surface of the ear canal. The balloon may contact the ear canal with sufficient force to keep the hearing aid from slipping along the length of the ear canal.

FIG. 14A shows a hearing aid with a balloon 1400 and a protruding portion 1402 within an ear canal 1404. In some embodiments, the balloon may contact that the ear canal surface at one or more point. In some embodiments, the balloon may contact the ear canal surrounding the hearing aid all around the hearing aid. The protruding portion may be provided to allow introduction or removal of the hearing aid within the ear canal. In some embodiments, the protruding portion may house electronic components therein. In some embodiments, the protruding portion may act as a passive amplifier. The balloon may be used as a securing mechanism in any other hearing aid configuration described elsewhere herein.

FIG. 14B a hearing aid with a balloon 1410 for bone conduction and a speaker 1420 for air conduction within an ear canal 1414. The balloon may optionally contact the surface of the ear canal at one or more point, or all around the ear canal surface surrounding the hearing aid. This configuration may advantageously allow sound to be transmitted via bone conduction and air conduction.

Figure 15:
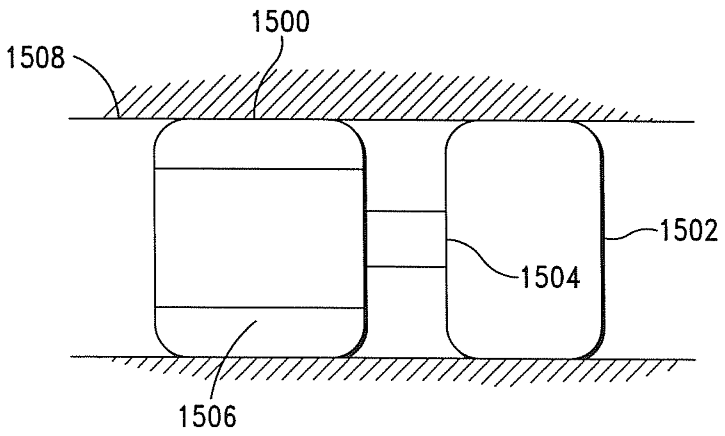
FIG. 15 provides an additional example of a hearing aid with a balloon configuration in an ear canal.

FIG. 15 provides an additional example of a hearing aid with a balloon configuration in an ear canal. The hearing aid may include one or more balloon for bone conduction 1500, one or more balloon for air conduction 1502, a speaker for higher frequencies (or another subset of frequencies) 1504, and a vibrating unit for other frequencies (or with overlap) 1506. The hearing aid may be provided with an ear canal 1508.

In some embodiments, higher frequencies of sound may be more effectively transmitted via air conduction and lower frequencies of sound may be more effectively transmitted via bone conduction. In some embodiments, the sound may be amplified as it is transmitted. For example, the bone conducting balloon may amplify vibrations transmitted to the bone while air conducting balloons and/or an additional passive amplifier may amplify vibrations transmitted to the eardrum.

In some embodiments, one or more balloon may contact a surface of the ear canal. The balloon for bone conduction and/or the balloon for air conduction may contact a surface of the ear canal. In some embodiments, the balloon for air conduction, may or may not contact the ear drum. The balloons may be filed with a fluid, such as a liquid, gel, or gas. In some embodiments, the balloons may have the same characteristics for bone conduction and air conduction. In other embodiments, the balloons may have different characteristics for bone conduction and air conduction. As previously mentioned, such characteristics may include balloon material, size, thickness, volume, pressure, or fluid.

In some embodiments, the hearing aid may have electronic components. In some embodiments, the electronic components-containing section may be surrounded by a balloon. The balloon may be a bone conducting balloon and may secure the hearing aid within the ear canal.

In some embodiments, a microphone may be an electronic component. The microphone may be in communication with the speaker. The microphone may be in electronic and/or mechanical communication with the speaker. Sound/vibrations picked up by the microphone may be transmitted to the speaker. In some embodiments, the sound/vibrations picked up may be amplified and transmitted to the speaker. In some embodiments, a passive amplifier may amplify the sound/vibrations transmitted to the speaker.

The speaker may be closer to the eardrum than the microphone. In some embodiments, the speaker may contact the eardrum or be in close proximity to the ear drum. The microphone may be external to the ear, or closer to ear canal opening. In some embodiments, distance may be provided between the speaker and microphone. In some embodiments, the distance may be greater than, less than, or fall between about 1 mm, 2 mm, 3 mm, 4 mm, 5 mm, 6 mm, 7 mm, 8 mm, 9 mm, 1 cm, 1.2 cm, 1.3 cm, 1.5 cm, 1.7 cm, 2 cm, 2.5 cm, 3 cm, 3.5 cm, 4 cm, 5 cm, 6 cm, or 7 cm.

In some embodiments, only one of the microphone or speaker may be provided in a main body of the hearing aid while the other is extended some distance away. For example, the microphone may be provided in a main body of the hearing aid while the speaker is extended toward the ear drum. Alternatively, the speaker may be provided in the main body while the microphone is extended away from the ear drum. Alternatively, both the microphone and speaker may be provided within the main body of the hearing aid.

The balloon assembly can contain one or more balloons. The balloons within the assembly can have different pressures, volumes, compliances of the membrane, viscosities, or contain different fluids. The balloon may also have one or more cavities or channels to allow for air to pass by it.

FIGS. 16A-16D show cross sections of various hearing aid securing mechanisms with different balloon or shaped configurations.

Figure 16A:
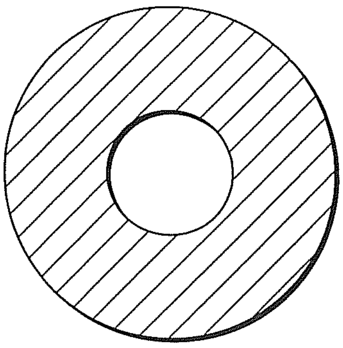
FIGS. 16A-16D show cross sections of various hearing aid securing mechanisms with different balloon or shaped configurations.

The balloon may fill the entire cross-sectional area of the ear canal (full-occlusion) or it may fill part of the cross-sectional area (partial-occlusion). For example, FIG. 16A shows a balloon that fully surrounds a central portion of a hearing device. The cross-sectional area may be filled by a combination of balloons and bristles.

Figure 16B:
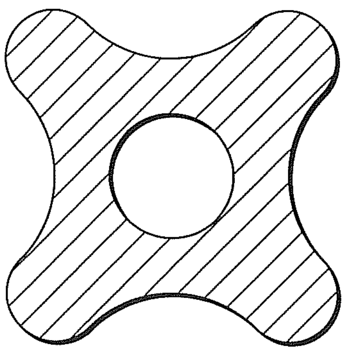
Figure 16C:
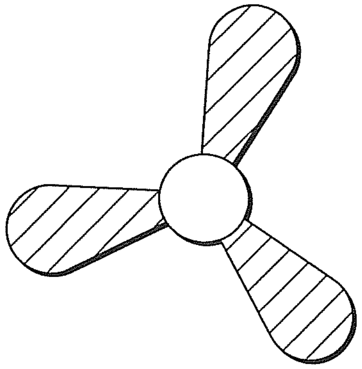
Figure 16D:
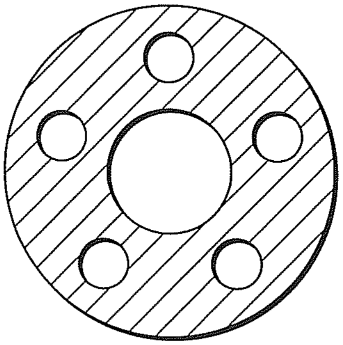

The partial-occlusion balloons may contain one or more lobes of a single balloon. FIG. 16B shows a balloon with four lobes. Any number of lobes may be provided, which may provide channels for air therebetween. Alternatively the balloon assembly can be made up of one or more separate balloons. FIG. 16C shows an example of a hearing aid with three separate balloons. Channels for air may be provided between the separate balloons. FIG. 16D provides an example of a single balloon that may have air channels passing through.

In one embodiment, the balloon membrane is made of materials of differing compliances. The most medial surface of the balloon is less compliant. This may allow for improved sound transmission to the air between the balloon and the tympanic membrane. The most lateral surface of the balloon may be more compliant. This may allow for absorption of sound such that there is less sound transmission lateral to the hearing aid components that may cause feedback problems. The most lateral (away from the tympanic membrane) surface of the balloon may also be a denser material to allow for a greater degree of reflection of sound waves.

There can be separate balloons for bone conduction and air conduction. In one embodiment the bone conduction balloon or balloons can be surrounding a vibrating unit of the hearing aid and the air conduction balloon or balloons can be facing the tympanic membrane and located more medially. Different balloons may have differing characteristics (fluid composition, density, pressure, shape, size) and be used to conduction different frequency ranges.

In addition to bristles and/or balloons, other securing mechanisms may be used to keep a hearing aid in place. Such securing mechanisms may include, but are not limited to bumps, protrusions, fringes, ridges of any orientation (e.g., lengthwise, radial, spiral), grooves, bubbles, hooks, tubes, or any other surface feature. The other securing mechanisms may have properties described for bristles or balloons herein. For example, the securing mechanisms may be adjustable. The angle, configuration, size, or volume may be adjustable.

Any components, features, characteristics, properties, or steps of other hearing aid devices may be incorporated into the embodiments described herein or used by the embodiments described herein. See, e.g., U.S. Pat. No. 6,137,889; U.S. Pat. No. 6,473,513; U.S. Pat. No. 6,940,989; U.S. Pat. No. 7,313,245; U.S. Pat. No. 5,259,032; U.S. Pat. No. 5,425,104; U.S. Patent Publication No. 2009/0052710; U.S. Pat. No. 5,031,219; which are hereby incorporated by reference in their entirety.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. An ear canal cleaning apparatus, comprising:

an elongated support member having a longitudinal axis, an outer surface and first and second ends; and a bristle member comprising a plurality of flexible elongated members configured to contact a surface of an ear canal, said bristle member being attached to said support member outer surface and proximate first end of said support member, said support member and bristle member assembly being configured to enter into an ear canal of a subject, each of said plurality of elongated members having first and second ends, said first ends being restrained proximate said support member outer surface and said second ends being unrestrained, said second ends being configured to provide a plurality of contact points when said securing member is disposed in said ear canal, each of said plurality of elongated members having a first length in the range of 0.1 mm-3 cm and a maximum thickness along said first length no greater than 3.0 mm, said plurality of elongated members being disposed circumferentially around said support member and projecting outwardly therefrom at an angle relative to said support member longitudinal axis in the range of approximately 5°-85°, whereby said second ends of said elongated members are directed toward said first end of said support member.

2. The ear canal cleaning apparatus of claim 1, wherein said plurality of elongated members comprises at least 3 of said plurality of elongated members.

3. The ear canal cleaning apparatus of claim 1, wherein said plurality of elongated members have a first cross sectional shape comprising a shape selected from the group consisting of a flat, round, elliptical, square, triangular and hexangular shape, and combinations thereof.

4. The ear canal cleaning apparatus of claim 1, wherein said support member comprises a flexible support member.

* * * * *